United States Patent [19]

Carlquist et al.

[11] Patent Number: 4,806,336

[45] Date of Patent: Feb. 21, 1989

[54] HUMAN INTESTINAL HORMONE AND ITS USE

[75] Inventors: Mats Carlquist; Hans Jörnvall, both of Sundbyberg, Sweden; Wolf-Georg Forssmann, Heidelberg, Fed. Rep. of Germany; Lars Thulin, Kristianstad, Sweden; Catja Johansson, Danderyd, Sweden; Viktor Mutt, Solna, Sweden

[73] Assignee: KabiGen AB and Skandigen AB, both of Stockholm, Sweden

[21] Appl. No.: 933,524

[22] PCT Filed: Mar. 7, 1986

[86] PCT No.: PCT/SE86/00099

§ 371 Date: Nov. 7, 1986

§ 102(e) Date: Nov. 7, 1986

[87] PCT Pub. No.: WO86/05494

PCT Pub. Date: Sep. 25, 1986

[30] Foreign Application Priority Data

Mar. 11, 1985 [SE] Sweden ............................ 8501202

[51] Int. Cl.$^4$ ..................... C07K 7/32; A61K 49/00; A61K 37/24

[52] U.S. Cl. ..................................... 424/9; 514/12; 514/21; 530/309; 530/324

[58] Field of Search ............... 530/309, 324; 514/21, 514/12; 424/9

[56] References Cited

U.S. PATENT DOCUMENTS 3,940,480  2/1976  Suenaga et al. .................. 424/177
4,533,494  8/1985  Uchiyama et al. ............... 530/309

FOREIGN PATENT DOCUMENTS 2323187  11/1973  Fed. Rep. of Germany.

OTHER PUBLICATIONS

Nilsson et al, Eur. J. Biochem., vol. 112, pp. 383–388 (1980).
Carlquist et al., Febs Letters, vol. 127, pp. 71–74 (1981).
Muckadell et al., Chem Abstr., vol. 96, No. 80352m (1982).
Carlquist et al, Chem. Abstr., vol. 103, No. 65113d (1985).
Carlquist et al., "Human Secretin is not Identical to the Porcine/Bovine Hormone", *IRCS Med. Sci.*, vol. 13, pp. 217–218 (1985).
Abstract Presented at the Sixth International Symposium on Gastrointestinal Hormones No. 148, Jul. 6–10, 1986.
Chem. Pharm. Bull., vol. 33, pp. 2000–2005, 1985, Uchiyama, M. et al, Studies on Secretin II, Synthesis of Secretin with High Activity.

Primary Examiner—Howard E. Schain
Assistant Examiner—Christina Chan
Attorney, Agent, or Firm—Burns, Doane, Swecker & Mathis

[57] ABSTRACT

A human intestinal hormone having the following peptide structure: His-Ser-Asp-Gly-Thr-Phe-Thr-Ser-Glu-Leu-Ser-Arg-Leu-Arg-Glu-Gly-Ala-Arg-Leu-G ln-Arg-Leu-Gln-Gly-Leu-Val-NH$_2$; compositions containing such hormone; and a method of stimulating pancreatic secretion.

4 Claims, 1 Drawing Sheet

His-Ser-Asp-Gly-Thr-Phe-Thr-Ser-Glu-Leu-Ser-Arg-Leu-(Arg)-Glu-Gly-Ala-(Arg)-Leu-Gln-(Arg)-Leu-Leu-Gln-Gly-(Leu)-(Leu)-(Val)-NH$_2$ 286 54 182 253 67 156 77 65 104 69 45 57 55 64 22 64 64 28

Fig. 1

HUMAN INTESTINAL HORMONE AND ITS USE

The present invention relates to human intestinal hormone, namely the hormone secretin which stimulates pancreatic secrection.

Secretin is an intestinal hormone formed by the mucosa of the upper portion of the small intestine, which stimulates the secretion of water and bicarbonate from the pancreas. The structure of porcine secretin has been known for some time and it has been isolated from porcine intestine and has been found to be constituted by a peptide composed of 27 amino acid residues (Mutt, V., Jorpes, J. E. and Magnusson, S. (1970) Eur. J. Biochem., 15, 513–519). Moreover, it has been found that bovine and porcine secretins are identical but that they are markedly different from chicken secretin (Carlquist, M., Jornvall, H. and Mutt, V. (1981) FEBS Lett., 127, 71–74).

Although bovine and porcine secretins behave identically with human secretin in some respects they are not structurally identical. In accordance with the instant invention it has now been found that amino acids number 15 and 16 differ in that the human secretin at said positions contains the residues of glutamic acid (Glu) and glycine (Gly), respectively. Thus, the human intestinal hormone of this invention has the peptide structure: His-Ser-Asp-Gly-Thr-Phe-Thr-Ser-Glu-Leu-Ser-Arg-Leu-Arg-Glu-Gly-Ala-Arg-Leu-Gln-Arg-Leu-Leu-Gln-Gly-Leu-Val-$NH_2$.

In the instant disclosure the abbreviations used for characterizing the amino acids and their residues are the traditional ones as found for example in the textbook Organic Chemistry, second edition, Ralph J. Fessenden & Joan S. Fessenden, Willard Grant Press, Boston, Mass., pages 852 and 853.

In the same way as the known secretins find diagnostic uses the human secretin according to this invention is highly useful in determining pancreatic and gallbladder functions. According to this aspect of the invention a composition for diagnostic use in this respect comprises an effective diagnostic amount of the secretin of this invention in combination with a carrier which does not interfere with the diagnostic procedure used.

The human secretin of this invention is in addition therapeutically useful in that it stimulates pancreatic secretion in man if administered in a suitable manner. According to this aspect of the invention a composition for such use is provided comprising an effective therapeutic amount of the human secretin of the invention in combination with a non-toxic, pharmaceutically acceptable carrier. In this context the invention also covers a method of treating gastro-intestinal disorders comprising administering a therapeutically effective amount of the hormone of this invention or a composition of this invention on a patient to be treated.

The present invention thus includes within its scope pharmaceutical compositions, which comprise the human intestinal hormone according to this invention in association with a pharmaceutically acceptable carrier. In clinical practice the compositions of the present invention will normally be administered parenterally due to the fact that being a peptide the hormone is sensitive to biologically active environments. Oral or rectal administration may, however, be conceivable using compositions of the slow release type making it possible for the active ingredient to reach the site of primary interest, namely the small intestine.

Preparations according to the invention for the preferred parenteral administration includes sterile aqueous or non-aqueous solutions, suspensions or emulsions. Examples of non-aqueous solvents or suspending media are propylene glycol, vegetable oils, such as olive oil, and injectible organic esters, such as ethyl oleate. These compositions may also contain adjuvants, such as preserving, wetting, emulsifying and dispersing agents. They may be sterilized, for example, by filtration through a bacteria-retaining filter, by incorporation of sterilizing agents in the composition, by irradiation or by heating. They may be also be manufactured in the form of sterile solid compositions, which can be dissolved in a sterile injectible medium immediately before use. As well as the more customary intravenous and intramuscular routes the compositions may also be administered by intraarticular injection.

The percentages of active ingredient in the compositions of the invention may be varied as long as they constitute a proportion such that a suitable dosage for the desired stimulatory effect on the pancreas is obtained. Obviously several unit dosage forms may be administered at about the same time. Generally, the compositions should contain from about 0.1% to about 80% by weight of active ingredient.

The dose employed depends upon the desired stimulatory effect, the route of administration and the duration of the treatment. The hormone of this invention may be administered each day or, according to the wishes of the medical practitioner, less often, e.g. weekly.

The invention will be further illustrated below in an example describing the isolation and characterization of the human secretin of this invention.

EXAMPLE

Pieces of human duodeni were obtained from patients undergoing surgery. The tissue was immediately rinsed and stored at −20° C. The combined frozen material (181 g wet weight) was immersed into boiling water for 10 min., cooled on ice, minced and extracted with 0.5M acetic acid (400 ml) for 16 h at 5° C. The suspension was filtered through Whatman 541 with the aid of 10 g Hyflo Super Cel. The filtrate was adjusted to pH 2.7 with 0.2M HCl and peptides were absorbed to alginic acid (40 g wet weight) during stirring for 1 h. The alginic acid was collected on a filter and successivley washed with ice-cold 0.005M Hcl, ethanol and again with the acid, whereafter peptides were eluted with ice-cold 0.2M HCl (190 ml). Sodium acetate was added to the eluate to pH 3.8 and peptides were precipitated with NaCl at saturation.

The precipitate obtained (460 mg) was dissolved in 4.6 ml water, diluted with two volumes of ethanol, brought to pH 7.2 with 0.3M NaOH and centrifuged. To the supernatant, two volumes of cold ethanol was added and the suspension was allowed to sediment at −20° C. for 24 h. The precipitate was removed by filtration and the filtrate was adjusted to pH 3.0 with 0.1M HCl. Peptides were recovered after addition of 100 ml methanol followed by three volumes of ether (Carlquist, M., Kaiser, R., Tatemoto, K., Jörnvall, H. and Mutt, V. (1984) Eur. J. Biochem., 144, 243–247.) This precipitate was dried under vacuum, dissolved in 1 ml 0.2M acetic acid and chromatographed on a Sephadex G-25 (fine) column (0.6×95 cm) in 0.2M acetic acid. Fractions of 1 ml were collected and tested in the secretin bioassay (Mutt, V. and Soderberg, U. (1959)

Arkiv. f. Kemi, 15, 63–68). The fractions containing the bulk of the secretin activity were combined and submitted to ion-exchange HPLC on an LKB TSK 535 CM column (7.5×150 mm) in a Waters instrument. Elution was performed with a gradient of sodium chloride (0.075–0.3M, 75 min) in a 0.02M sodium phosphate buffer, pH 6.4, at 1 ml/min and fractions of 1 ml were collected. Final purification was carried out by reverse-phase HPLC using an LKB TSK ODS-120T column (4.6×250 mm). Elution was performed with a gradient of acetonitrile (25–50%, 50 min) in 0.1% trifluoroacetic acid at 1 ml/min (Carlquist, M. and Rökaeus, Å. (1984) J. Chromatogr. 296, 143–151).

Hydrolysis was carried out for 24 h at 110° C. in evacuated tubes with 6M HCl containing 0.5% phenol. Amino acides were analyzed by reverse-phase HPLC after precolumn derivatization with phenylisothiocyanate (Koop, D. R., Morgan, E. T., Tarr, G. E. and Coon, M. J. (1982) J. Biol. Chem. 257, 8472–8480).

Edman degradation of the peptide was performed with an Applied Biosystems Model 470A gas-phase sequence and amino acid derivatives were analyzed by HPLC (Zimmerman, C. L., Apella, E. and Pisano, J. J. (1977) Anal. Biochem. 77, 569–573).

RESULTS

The isolation procedure described above, starting with 181 g tissue, resulted in 500 pmol secretin. Through all steps up to and including the ion-exchange step, the material behaved identically to porcine/bovine secretin. However, on the $C_{18}$ column, the elution time for the human hormone was not identical to that of the porcine. These findings indicate that human and porcine secretins are not identical, although they have the same net charge.

The result of the amino acid analysis, performed on 20 pmol, is shown in Table 1 as enclosed hereto. Like porcine secretin, human secretin is composed of 27 amino acid residues, but with a different composition. Differences are seen for position 15, Asp (−1), Glu (+1) and position 16, Ser (−1) and Gly (+1).

The amino acid sequence of the human secretin of this invention is shown in appended FIG. 1. The figure shows gas-phase sequence degradation of 450 pmoles of the intact peptide. The values shown constitute pmoles recovered. Residues within parenthesis are not fully identified. Repetitive yield calculated on $Leu_{10-22}$ is 96%.

The structure shown in FIG. 1 differs from that of porcine/bovine secretin at positions 15 and 16, by having Glu-15 and Gly-16 instead of Asp-15 and Ser-16. This is in full agreement with the amino acid analysis and explains the observations during the isolation.

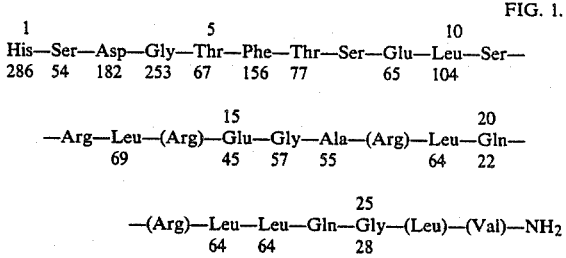

FIG. 1.

TABLE 1

| | Amino acid composition of human secretin | |
|---|---|---|
| Amino acid | Human secretin | Porcine/bovine secretin |
| Asp | 1.0 (1) | 2 |
| Glu | 4.0 (4) | 3 |
| Ser | 2.7 (3) | 4 |
| Gly | 3.1 (3) | 2 |
| His | 1.1 (1) | 1 |
| Thr | 2.0 (2) | 2 |
| Ala | 1.2 (1) | 1 |
| Arg | 3.7 (4) | 4 |
| Val | 1.3 (1) | 1 |
| Leu | 5.7 (6) | 6 |
| Phe | 1.0 (1) | 1 |
| Total | 27 | 27 |

We claim:

1. A human intestinal hormone in isolated form having the following peptide structure: His-Ser-Asp-Gly-Thr-Phe-Thr-Ser-Glu-Leu-Ser-Arg-Leu-Arg-Glu-Gly-Ala-Arg-Leu-Gln-Arg-Leu-Leu-Gln-Gly-Leu-Val-$NH_2$.

2. A composition for use in stimulating pancreatic secretion in man or for diagnostic use in determining pancreatic or gallbladder function comprising an effective therapeutic amount or an effective diagnostic amount of the hormone of claim 1 in combination with a non-toxic carrier therefore.

3. A method for diagnosing a problem in pancreatic or gallbladder function, said method comprising administering to a patient in need of such diagnosis a diagnostic amount of the hormone of claim 1.

4. A method for stimulating pancreatic secretion in man, said method comprising administering to a patient in need of such treatment a pancreatic secretion stimulating amount of the hormone of claim 1.

* * * * *